(12) United States Patent
Bortolin et al.

(10) Patent No.: US 9,795,796 B2
(45) Date of Patent: Oct. 24, 2017

(54) IMPLANTABLE ELECTRONIC DEVICE EMPLOYING FUSED THERMOPLASTIC-CONDUCTOR SUBASSEMBLY AND METHOD OF MANUFACTURING THE SUBASSEMBLY AND THE DEVICE

(71) Applicant: PACESETTER, INC., Sylmar, CA (US)

(72) Inventors: Dino Bortolin, Camarillo, CA (US); Ofer Rosenzweig, Chatsworth, CA (US); Christopher R. Jenney, Valencia, CA (US); Avi Bilu, Pasadena, CA (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 15/076,300

(22) Filed: Mar. 21, 2016

(65) Prior Publication Data

US 2017/0056675 A1  Mar. 2, 2017

Related U.S. Application Data

(60) Provisional application No. 62/209,767, filed on Aug. 25, 2015.

(51) Int. Cl.
*A61N 1/00* (2006.01)
*A61N 1/375* (2006.01)
*A61B 5/0402* (2006.01)
*A61B 5/00* (2006.01)

(52) U.S. Cl.
CPC .......... *A61N 1/3752* (2013.01); *A61B 5/0402* (2013.01); *A61B 5/686* (2013.01); *A61B 2562/22* (2013.01)

(58) Field of Classification Search
CPC ... A61B 2562/22; A61B 5/0402; A61B 5/686; A61N 1/3752
See application file for complete search history.

(56) References Cited

U.S. PATENT DOCUMENTS 7,615,012 B2 * 11/2009 Von Arx ................ A61B 7/023
600/528
8,103,348 B1 * 1/2012 Coffed ................ A61N 1/3752
607/37

\* cited by examiner

*Primary Examiner* — George Manuel (57) ABSTRACT

Disclosed herein is an implantable electronic device. The device has a housing and a header connector assembly coupled to the housing. The header connector assembly has a connector assembly and a header enclosing the connector assembly. The connector assembly has a subassembly including an electrically conductive component at least partially residing within a first material that is provided about the electrically conductive component. The header has a second material that is provided about the connector assembly and the subassembly subsequent to the first material setting up about the electrically conductive component.

8 Claims, 10 Drawing Sheets

IMPLANTABLE ELECTRONIC DEVICE EMPLOYING FUSED THERMOPLASTIC-CONDUCTOR SUBASSEMBLY AND METHOD OF MANUFACTURING THE SUBASSEMBLY AND THE DEVICE

CROSS-REFERENCE TO RELATED PATENT APPLICATIONS

This application claims priority to U.S. Provisional Patent Application Ser. No. 62/209,767, filed Aug. 25, 2015, titled "Method for Creating a Fused Thermoplastic-Conductor Subassembly for use in Manufacturing an IPG Header," and is hereby incorporated herein by reference in its entirety.

FIELD OF THE INVENTION

Aspects of the present invention relate to medical apparatus and methods. More specifically, the present invention relates to systems and methods for manufacturing a header connector assembly of an implantable electronic device such as an implantable pulse generator or implantable cardiac monitor.

BACKGROUND OF THE INVENTION

Implantable electronic devices (IEDs) include pulse generators (IPGs) such as pacemakers and implantable cardioverter defibrillators (ICDs), which are used in the treatment of cardiac conditions, and neuromodulators or neurostimulators, which are used in chronic pain management or the actuation and control of other body systems. These IPGs commonly include a housing, feedthrus, and a connector assembly that is enclosed in a header. Electrical stimulation originating in the housing is led to the connector assembly through feedthrus. The connector assembly serves to transmit electrical signals out of the IPG and to a lead electrically connected to the connector assembly, the lead transmitting electrical signals between the IPG and patient tissue.

Other IEDs include implantable cardiac monitors (ICMs), which also employ a housing and a header. ICMs are used to monitor heart function or other electrical signals, but do not administer electrotherapy.

A header of an IED encloses the connector assembly, which has many internal electrically conductive components such as, for example, wires, ribbon, antennas, blocks, rings, etc. In order for the IED to have proper functionality when implanted, certain spacing between the electrically conductive components of the connector assembly should be maintained during installation into the header, regardless of whether the header and connector assembly are joined together via a cast-in-place process, an injection molding process or any other type of process. Accordingly, there is a need in the art for an IED with more reliably spaced connector assembly components and a method of manufacturing offering improved reliability with respect to component spacing.

BRIEF SUMMARY OF THE INVENTION

Disclosed herein is an implantable electronic device. In one embodiment, the device includes a housing and a header connector assembly coupled to the housing. The header connector assembly includes a connector assembly and a header enclosing the connector assembly. The connector assembly includes a subassembly including an electrically conductive component at least partially residing within a first material that was provided about the electrically conductive component. The header includes a second material that was provided about the connector assembly and the subassembly subsequent to the first material setting up about the electrically conductive component.

In one embodiment, the first material includes a thermoplastic. The thermoplastic may have been provided via melting. The melting may have been brought about via at least one of inductive heating, Ohmic heating or laser heating of the electrically conductive component. The thermoplastic may include at least one of TECOTHANE, PELLETHANE, BIONATE or ELASTHANE. The subassembly may be a fused thermoplastic-conductor subassembly. The second material may include epoxy, silicone rubber, polyurethane, TECOTHANE, PELLETHANE, BIONATE, or ELASTHANE. The second material may be provided via at least one of a backfilling process, an overmolding process, an injection molding process, or a casting process. The electrically conductive component includes at least one of a wire, ribbon, antenna, block, or ring.

Depending on the embodiment, the implantable electronic device may include an implantable pulse generator for administering electrotherapy via an implantable medical lead configured to couple with the implantable pulse generator. Alternatively, the implantable electronic device may include an implantable cardiac monitor.

Also disclosed herein is a method of manufacturing an implantable electronic device. In one embodiment, the method includes: forming a fused thermoplastic-conductor subassembly by causing an electrically conductive component of a connector assembly of a header connector assembly to fuse to a thermoplastic; and forming a header of the header connector assembly about the fused thermoplastic-conductor subassembly.

In one embodiment, the fusing is brought about by melting the thermoplastic via at least one of inductive heating, Ohmic heating or laser heating of the electrically conductive component. The thermoplastic may include at least one of TECOTHANE, PELLETHANE, BIONATE, or ELASTHANE. The electrically conductive component may include at least one of a wire, ribbon, antenna, block, or ring. The header may be formed about the thermoplastic-conductor subassembly via at least one of a backfilling process, an overmolding process, an injection molding process, or a casting process.

In one embodiment, the thermoplastic includes at least two opposed portions and the electrically conductive component is sandwiched between the two opposed portions prior to the electrically conductive component being fused to the thermoplastic. The sandwiched opposed portions and electrically conductive component may be compressed between pressure platens when the electrically conductive component is being fused to the thermoplastic.

In one embodiment, the thermoplastic is placed on a single side of the electrically conductive component, which is maintained in close intimate contact with the thermoplastic when the electrically conductive component is being fused to the thermoplastic.

The method of manufacturing may be employed in the manufacture of an implantable electronic device including an implantable pulse generator for administering electrotherapy via an implantable medical lead configured to couple with the implantable pulse generator. The method of manufacturing may also be employed in the manufacture of an implantable electronic device comprises an implantable cardiac monitor.

In one embodiment of a method of fabricating a thermoplastic-conductor subassembly for IPG headers, the method includes molding one thermoplastic component or two mating thermoplastic components. The one or more thermoplastic components are assembled with one or more metallic multi-path conductor components. The thermoplastic component(s) and the metallic multi-path conductor component(s) are then compressed together using a fixture or mold while the conductors are heated by inductive methods, Ohmic heating, or laser absorption. The heat generated within the conductors will reflow the thermoplastic material local to the conductors, resulting in a fused, rigid sub-assembly incorporating the internal electrical components. This sub-assembly will ensure proper positioning of the internal conductor components in the subsequent casting or overmolding operations necessary to complete the IPG header.

In one embodiment, the thermoplastic-conductor subassembly starts out as two independent support structures, namely, a first molded split web and a second molded split web, each of which are made with conventional thermoplastic injection molding techniques. The first molded split web is then placed into a first pressure platen, and the second molded split web is placed into a second pressure platen. The conductor elements are then placed between the first and second molded split webs and, more specifically, in one embodiment, on top of one of the molded split webs.

The positional accuracy of the placement of the conductor elements is dictated by features on the platen. The features will vary depending on conductor/antenna configuration (e.g., flat ribbons, antennas, and/or round wire). Once the conductor elements are in place between the two molded split webs and the two pressure platens holding the respective molded split webs, the two pressure platens are joined. The pressure platens are brought together at a predetermined force and the conductors (e.g., flat ribbons, antennas, and/or round wire) are heated by inductive methods, Ohmic heating (e.g., passing current), laser energy, or other heating methods.

In one embodiment for applying electrical current to the conductors to induce Ohmic heating, contacts are made by pogo pins on one pressure platen, which are then connected to a power supply. Additional circuitry or controlling elements as known in the art can be used to ensure proper current and voltage to each conductive element. No matter whether Ohmic, inductive, or laser heating methods are used, the resulting elevated temperature softens the material surrounding the conductors while the pressure forces the materials to come in contact with one another, fusing the two molded split webs together and encapsulating the conductor(s) and/or antennas. After the heating is turned off and the resulting thermoplastic-conductor subassembly has cooled, the platens are opened and the thermoplastic-conductor subassembly can be removed.

In one embodiment of a method of fabricating a thermoplastic-conductor subassembly for IPG headers, the method includes fusing a single piece thermoplastic structure to conductor elements to create the thermoplastic conductor subassembly. The thermoplastic material, although fused to the conductor elements, may or may not completely encapsulate the conductor elements.

A single injection molded plate made of a thermoplastic, such as, for example, TECOTHANE, PELLETHANE, BIONATE, ELASTHANE, or etc., is provided. The conductor elements are welded to their respective ring and tip connector blocks. The thermoplastic plate is placed in intimate contact with the conductor elements and/or portions of the blocks. Application of pressure platens or other fixtures may be employed to ensure the intimate contact. The metal conductors are then heated by, for example, inductive, Ohmic, laser, or other heating processes in order to locally melt the thermoplastic plate, bonding it to the conductor elements and/or portions of the blocks. The resulting fused thermoplastic-conductor subassembly ensures no movement of the conductors during subsequent overmolding by conventional injection molding or casting operations necessary to complete the header.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION

Implementations of the present disclosure involve an implantable electronic device (IED) such as an implantable cardiac monitor (ICM) or an implantable pulse generator (IPG). The IPG administers electrotherapy or other neurostimulation via an implantable lead having a lead connector end on a proximal end of the implantable lead. The IPG includes a housing or can and a connector assembly enclosed in a header to form a header connector assembly that is coupled to the housing or can. The header connector assembly has at least one lead connector receiving bore or receptacle that includes electrical contacts of the connector assembly that make electrical contact with corresponding electrical terminals on the lead connector end on the proximal end of the implantable lead when the lead connector end is plugged into or otherwise received in the lead connector receiving bore or receptacle. Via the electrical connection between the corresponding electrical terminals of the lead connector end and the electrical contacts of the lead connector receiving bore, electrical signals can be administered from the IPG and through the lead to patient tissue. Similarly, but in reverse, electrical signals originating in patient tissue can travel via the lead to the IPG to be sensed at the IPG.

The ICM is similar to the IPG in that it also includes a housing or can and a header. However, unlike the IPG, the ICM does not attach to leads and the ICM simply monitors electrical signals and does not administer therapy.

The implantable electronic device configurations and methods of assembly disclosed herein are advantageous for at least the reason that they save costs and provide improvements to quality control. Specifically, the implantable electronic devices disclosed herein employ a fused thermoplastic-conductor subassembly 65 that maintains a desired spacing between the conductor elements 64 of the subassembly 64. This desired spacing is a preferred spacing for assembling the connector assembly 42 into the header 40 to form the header connector assembly 22.

Before beginning a detailed discussion of fused thermoplastic-conductor subassemblies 65 and the corresponding methods of manufacture, a general discussion is first given regarding features of a common lead connector end at the proximal end of an implantable medical lead followed by a general discussion of the features of an IPG. While the following discussion of the implantable electronic device is given in the context on an IPG, it can be readily understood by those of skill in the art that the discussion is applicable to an ICM for the pertinent aspects of this disclosure.

A. Overview of Common Lead Connector End and IPG

Figure 1:
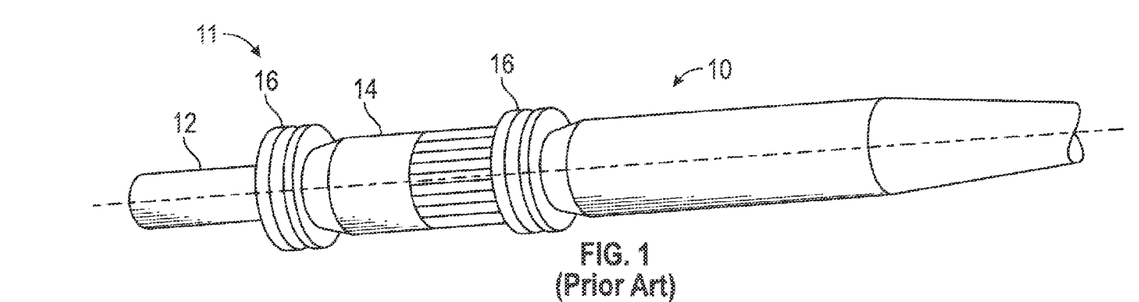
FIG. 1 is an isometric view of a proximal end portion (i.e., lead connector end) of a conventional transvenous bipolar pacing lead.

FIG. 1 shows a proximal end portion 10 of a conventional transvenous, bipolar pacing lead, but is generally representative of any type of implantable lead whether in the cardiac, pain management or other medical treatment space. The diameter of such a lead may be made a sufficiently small diameter to facilitate the lead's implantation into small veins such as those found in the coronary sinus region of the heart and to allow implantation of a plurality of leads into a single vessel for multi-site or multi-chamber pacing. It should be understood, however, that other lead designs may be used, for example, multipolar leads have proximal ends portions that are bifurcated, trifurcated or have other branched configurations. While the lead whose proximal end is shown in FIG. 1 is of the bipolar variety, there are unipolar leads that carry but a single electrode, and multipolar leads that have more than two electrodes.

As is well known in the art, bipolar coaxial leads typically consists of a tubular housing of a biocompatible, biostable insulating material containing an inner multifilar conductor coil that is surrounded by an inner insulating tube. The inner conductor coil is connected to a tip electrode on the distal end of the lead. The inner insulating tube is surrounded by a separate, outer multifilar conductor coil that is also enclosed within the tubular housing. The outer conductor coil is connected to an anodal ring electrode along the distal end portion of the lead. The inner insulation is intended to electrically isolate the two conductor coils preventing any internal electrical short circuit, while the housing protects the entire lead from the intrusion of body fluids. These insulating materials are typically either silicone rubber or polyurethane. More recently, there have been introduced bipolar leads in which multifilar cable conductors contained within multilumen housings are substituted for the conductor coils in order to reduce even further the overall diameter of the lead.

The proximal lead end portion 10 shown in FIG. 1 includes a lead connector end 11 that conforms to the IS-1 standard, comprising a pair of coaxial spaced-apart electrical terminals including a tip terminal 12 and a ring terminal 14. The tip terminal 12 is electrically connected by means of the inner conductor coil to the tip electrode at the distal end of the lead, while the ring terminal 14 is electrically connected to the anodal ring electrode by means of the outer conductor coil. The tip and ring terminals of the lead connector end may each be engaged by a conductive garter spring contact or other resilient electrical contact element in a corresponding lead connector receiving bore of the header, the resilient electrical contact element being carried by a connector assembly enclosed in the header as described below. The lead connector end 11 on the proximal lead end portion 10 further comprises spaced-apart pairs of seal rings 16 for abutting against in a fluid-sealing manner the inner circumferential surface of the lead connector receiving bore of the header, thereby preventing body fluids from reaching the electrical terminals and contacts when the lead connector end 11 is plugged into the corresponding lead connector receiving bore. With the lead connector end 11 of the lead inserted in the lead connector receiving bore of the header and connector assembly, the tip and ring terminals 12 and 14 are electrically coupled via the contacts of the connector assembly and a feedthru to the electronic circuits within the hermetically sealed housing of the IPG (e.g., cardiac pacemaker, ICD, or other implantable tissue stimulation and/or sensing device such as those used in pain management, etc.).

Figure 2:
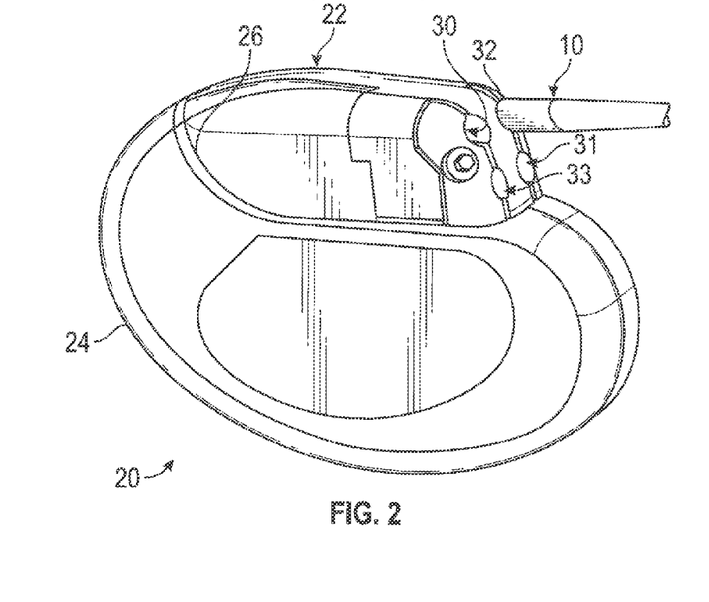
FIG. 2 is an isometric view of a cardiac pacemaker/defibrillator unit (i.e., implantable pulse generator (IPG)) incorporating connector junctions or terminals for communication with one or more electrodes.

FIG. 2 shows a multi-site or multi-chamber cardiac pacemaker/defibrillator unit that is generally representative of any type of IPG 20 incorporating a header connector assembly 22 coupled to a housing 24. The header connector assembly 22 includes a header 40 enclosing a connector assembly 42, both of which are depicted respectively in FIGS. 3, 4A and 4B discussed below. The IPG 20 is of a conventional design, including a hermetically sealed housing 24, which is also known as a can or casing. The housing 24 encloses the electronic components of the IPG 20 with the header connector assembly 22 mounted along a top surface 26 of the housing 24.

FIG. 2 illustrates that, in some embodiments, the header connector assembly 22 may include four or more lead connector receiving bores or receptacles 30, 31, 32 and 33 for receiving the lead connector ends of four implantable leads. FIG. 2 also shows the proximal end portion 10 of a lead, wherein the lead connector end on the proximal end portion 10 of the lead is received in a corresponding receptacle 32. In other embodiments, the header connector assembly 22 includes two receptacles comprising a single pair of receptacles (i.e., receptacles 30 and 33) for receiving the proximal ends of leads such as, for example, conventional bipolar leads and/or conventional cardioverting and/or defibrillating leads.

Figure 3:
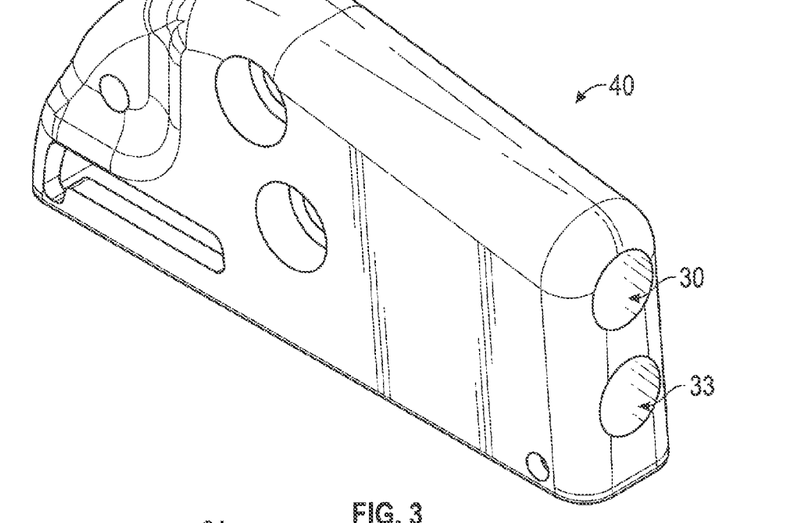
FIG. 3 is an isometric view of a representative header.
Figure 4A:
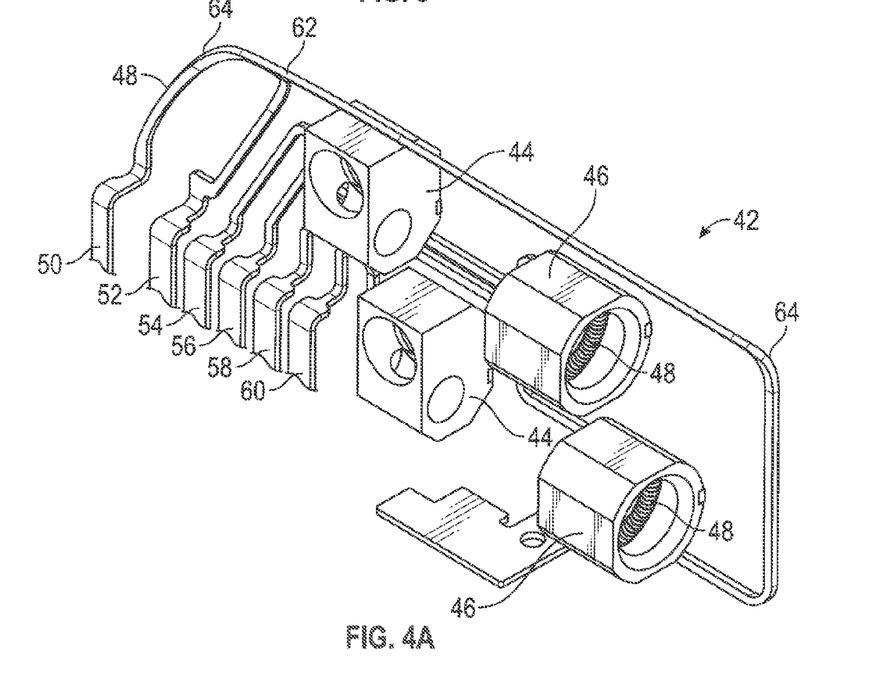
FIGS. 4A and 4B are opposite isometric views of a representative connector assembly used with the header of FIG. 3 to form a header connector assembly.
Figure 4B:
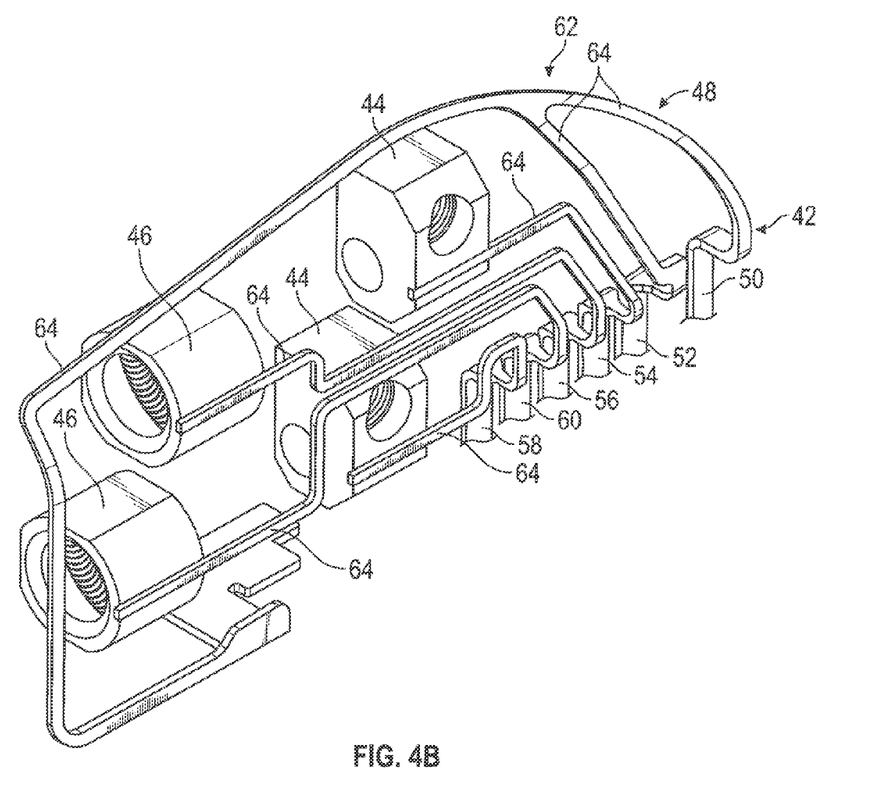

FIG. 3 is an isometric view of a representative header 40, and FIGS. 4A and 4B are opposite isometric views of a representative connector assembly 42. Unlike the header connector assembly 22 of FIG. 2, the header 40 of FIG. 3 only has a single pair of receptacles 30 and 33. However, in other embodiments, the header 40 of FIG. 3 may have two or more pairs of receptacles similar to the embodiment of FIG. 2.

As illustrated in FIGS. 4A and 4B, the connector assembly 42 includes tip blocks 44 and ring blocks 46. The ring blocks 46 include spring contacts 48. Each electrical block 44 and 46 of the connector assembly 42 serves as an electrical contact of the connector assembly 42. Thus, as can be understood from FIGS. 1-4B, each tip block 44 is configured to receive and make electrical contact with the tip terminal 12 of a lead connector end 11 received in the corresponding receptacle 30, 33 of the header 40. Similarly, each ring block 46 is configured to receive and make electrical contact with the ring terminal 14 of a lead connector end 11 received in the corresponding receptacle 30, 33 of the header 40. While the connector assembly 42 of FIGS. 4A and 4B is of an IS-1 configuration, other configurations (e.g., IS-4, etc.) are used in other embodiments. While the connector assembly 42 of FIGS. 4A and 4B only depicts two pairs of blocks 44, 46, in other embodiments where the header includes more than a single pair of receptacles 30, 33 (e.g., two pairs of receptacles 30, 31, 32, 33 as indicated in FIG. 2), the connector assembly 42 will have a four pairs of blocks 44, 46.

As shown in FIGS. 4A and 4B, the connector assembly 42 also includes a host of electrically conductive components including an antenna 48, a an RF anchor tab 50, an RF pin tab 52, an A-tip tab 54, an A-ring tab 56, an RV-ring tab 58, an RV-tip tab 60, and a ribbon carrier 62 and other conductors 64 that extend between the various tabs and their respective electrical contacts of the connector assembly or other components thereof. In other words, as can be understood from FIGS. 4A and 4B, electrical conductor elements (e.g., wires, traces, or other electrical conductors) 64 extend between the electrical blocks 44, 46 and the respective tabs 50, 52, 54, 56, 58 and 60. Also, such conductor elements 64 may form the antenna 48 and the ribbon carrier 62.

The various tabs are welded to corresponding terminals extending from circuitry of the IPG 20 contained in the housing 24 of the IPG 20 depicted in FIG. 2 when the connector assembly 22 is joined with the housing 24 to form the IPG 20. The connector assembly 42 is manufactured of materials and via methods known in the industry. The connector assembly 42 is cast in place, injected molded or otherwise installed into the header 40 to form the header connector assembly 22 of FIG. 2, which can be considered a first module that is then attached via a backfill or other process to a second module in the form of the housing 24. In other words, the header connector assembly 22 (i.e., first module) is attached via a backfill or other process to the housing 24 (i.e., the second module) to form the IPG 20.

In order for the IPG 20 to have proper functionality when implanted, certain spacing between the electrically conductive components of the connector assembly 42 should be maintained during the installation of the connector assembly 42 into the header 40. A fused thermoplastic-conductor subassembly 65 can be employed to maintain the desired spacing. This thermoplastic-conductor subassembly 65 and its method of manufacture and use will now be discussed in detail.

B. Thermoplastic-Conductor Subassemblies and Methods of Manufacture and Use

Figure 5:
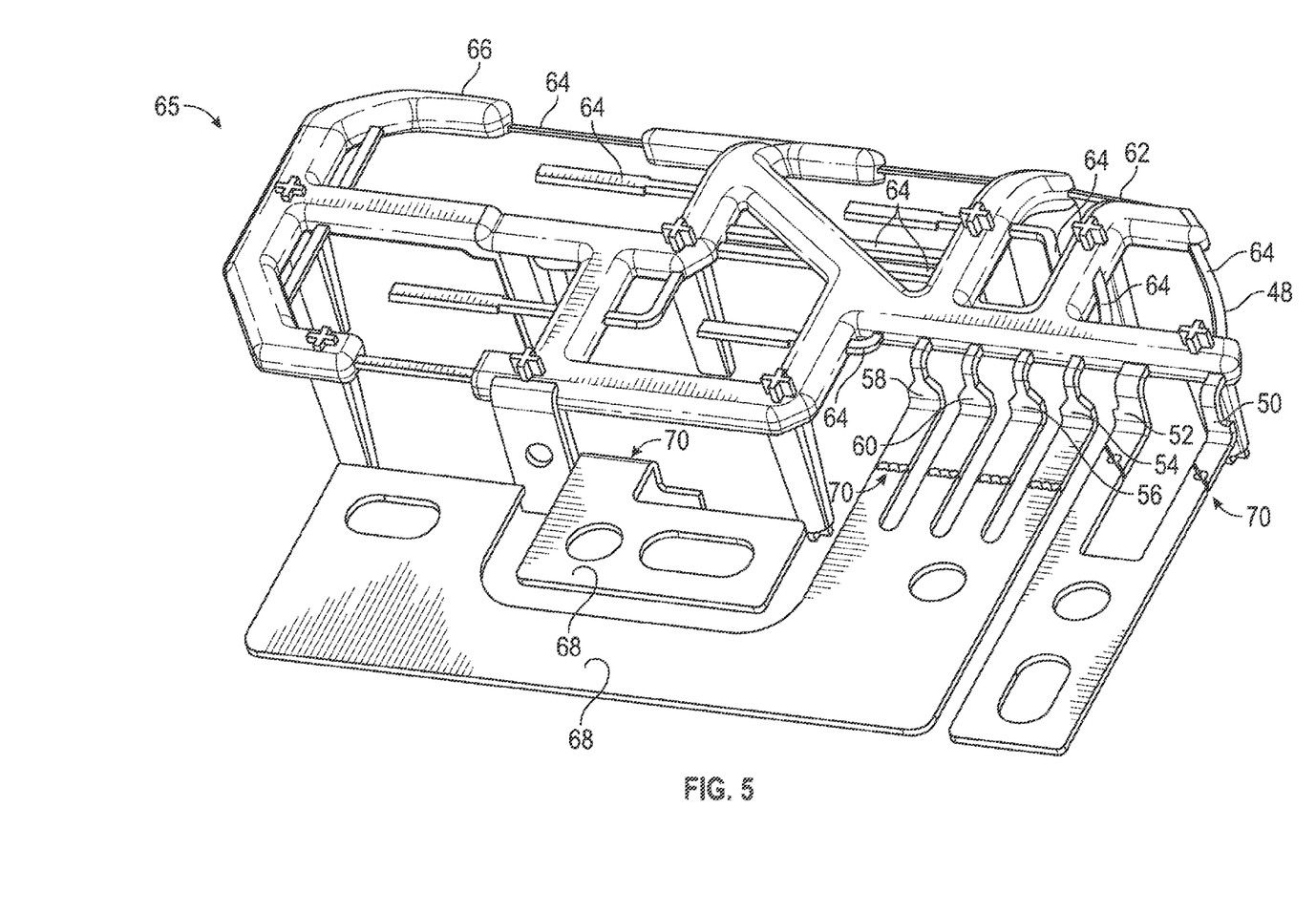
FIG. 5 is an isometric view of a fused thermoplastic-conductor subassembly.

FIG. 5 is an isometric view of a fused thermoplastic-conductor subassembly 65. As illustrated in FIG. 5, the subassembly 65 includes the electrical conductor elements (e.g., wires, traces, or other electrical conductors) 64 associated with the antenna 48, RF anchor tab 50, RF pin tab 52, A-tip tab 54, A-ring tab 56, RV-ring tab 58, RV-tip tab 60, and ribbon carrier 62 of the connector assembly 42 of FIGS. 4A-4B, plus a thermoplastic structure 66 encapsulating portions of the conductor elements 64 at certain locations of the conductor elements 64 and thereby maintaining a desired spacing between the conductor elements 64. The desired spacing between the conductor elements 64 that is maintained via the thermoplastic structure 66 is one that is preferred during the manufacturing of the connector assembly 42 from the conductor elements 64 and the combining of the connector assembly 42 with the header 40 of the header connector assembly 22 to form the header connector assembly 22, the combining of the connector assembly 42 with the header 40 involving a backfilling process, an overmolding process, an injection molding process or another manufacturing process.

Figure 6:
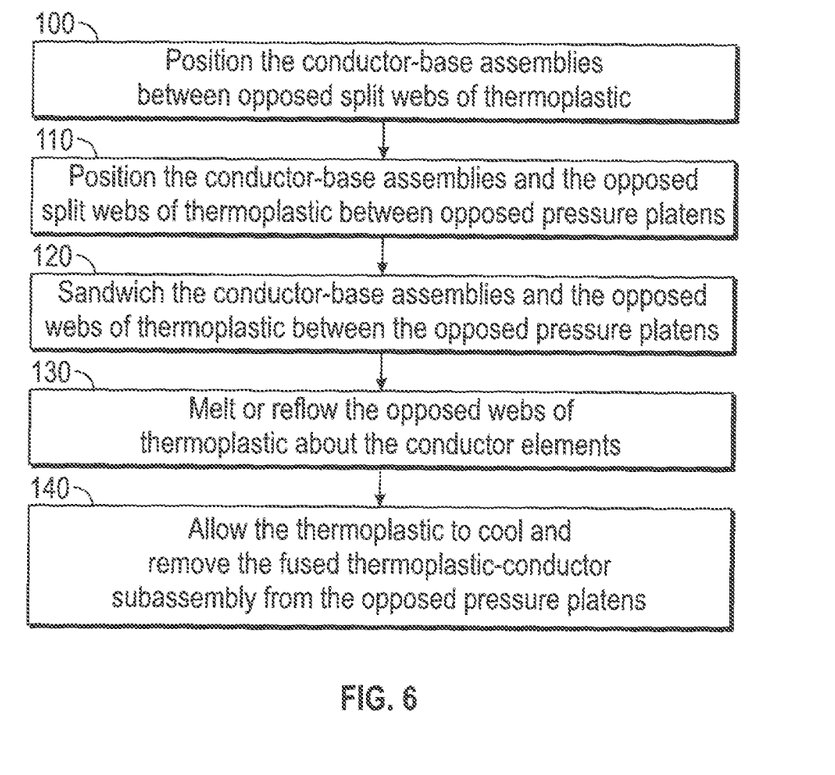
FIG. 6 is a flow chart outlining a method of manufacturing the fused thermoplastic-conductor subassembly of FIG. 5.
Figure 7:
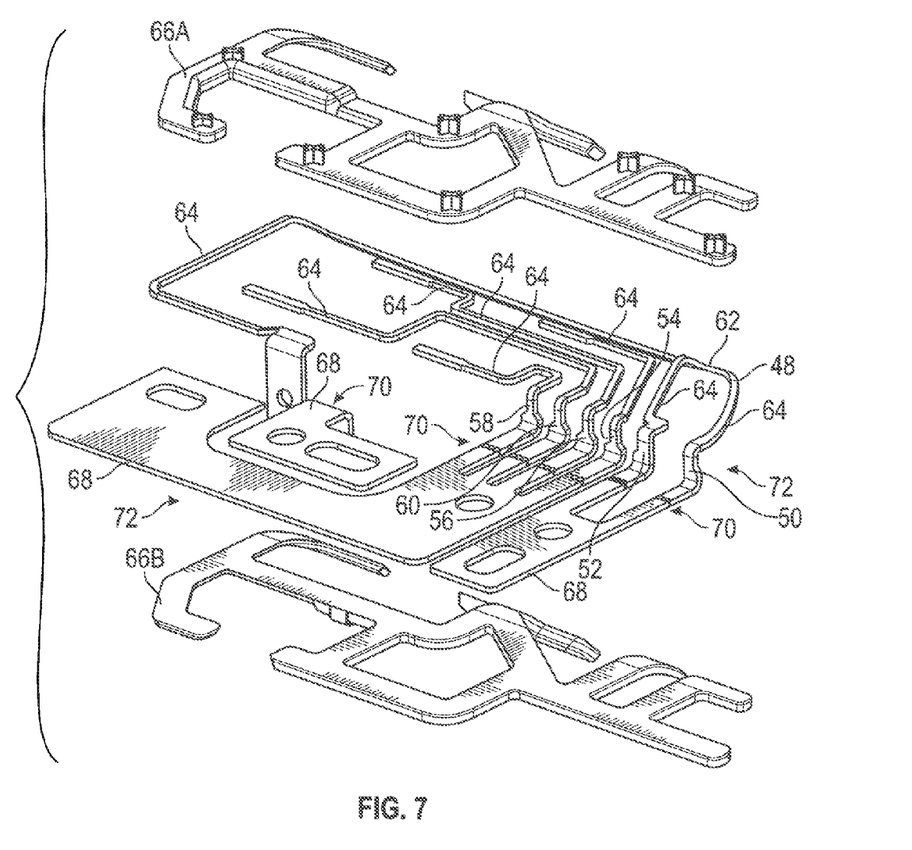
FIG. 7 is the same view as FIG. 5, except the thermoplastic structure of FIG. 5 is in the form of two split webs that are positioned on either side of the conductor elements to be fused together about the conductor elements.

To begin a discussion of the manufacture of the fused thermoplastic-conductor subassembly 65 of FIG. 5, reference is made to FIGS. 6 and 7. FIG. 6 is a flow chart outlining the manufacturing process, and FIG. 7 is the same view as FIG. 5, except the thermoplastic structure 66 of FIG. 5 is in the form of two split webs 66A, 66B that are positioned on either side of the conductor elements 64 to be fused together about the conductor elements 64 as shown in FIG. 5 and as discussed below. As can be understood from FIGS. 5 and 7, the conductor elements 64 are initially maintained in position relative to each other via regions or bases 68 of excess or scrap conductive material from which the conductor elements 64 are printed, etched, stamped, etc. These excess or scrap regions or bases 68 are removed from the conductor elements 64 at separation lines 70 at a point in the assembly subsequent to the fusing of the webs 66A, 66B about the conductor elements 64. For purposes of this discussion, when the conductor elements 64 are positioned relative to each other via the attached regions or bases 68 prior to the regions or bases 68 being removed from the conductor elements 64, the combined conductor elements 64 and regions or bases 68 are referred to herein as a conductor-base assemblies 72.

As can be understood from FIGS. 6 and 7, in one embodiment, the conductor-base assemblies 72 are positioned between the opposed split webs 66A, 66B [block 100]. More specifically, the conductor-base assemblies 72 are positioned between the opposed split webs 66A, 66B such that the conductor elements 64 are located between the opposed split webs and will be sandwiched between split webs when the split webs are brought together. The split webs 66A, 66B may be formed of thermoplastic materials such as, for example, TECOTHANE, PELLETHANE, BIONATE, ELASTHANE, or etc.

Figure 8:
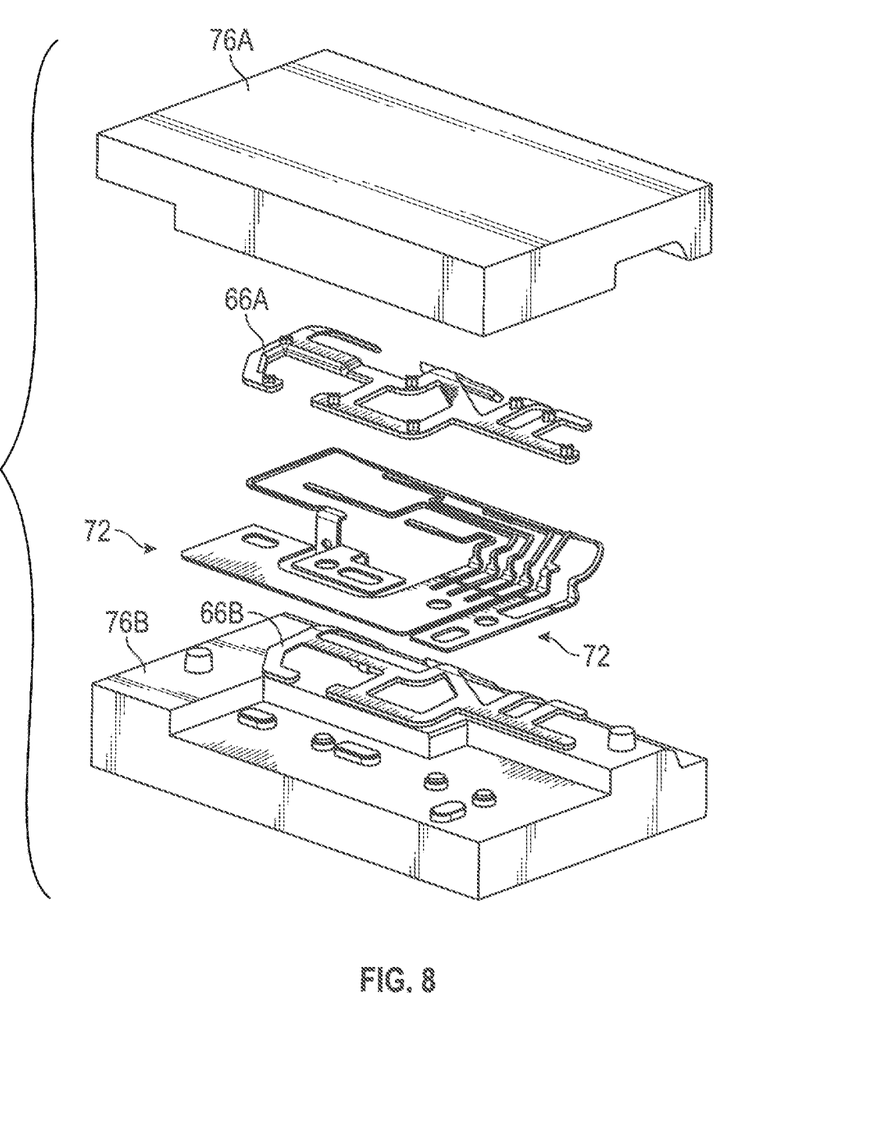
FIG. 8 is the same view as FIG. 7, except further along in the manufacturing process outline in FIG. 6 and wherein pressure platens have been introduced to compress together the conductor elements and the thermoplastic split webs.

As illustrated in FIG. 8, which is the same view as FIG. 7, except further along in the process, the opposed split webs 66A, 66B and the conductor-base assemblies 72 are located between opposed pressure platens 76A, 76B of a mold or fixture [block 110]. The opposed split webs 66A, 66B and the conductor-base assemblies 72 are then sandwiched between the pressure platens 76A, 76B [block 120]. The thermoplastic material of the opposed split webs 66A, 66B is melted or caused to reflow about the conductor elements 64, thereby imbedding the conductor elements 64 in the thermoplastic material in at least a few locations on the conductor elements and causing the opposed split webs to fuse to each other and with the conductor elements [block 130]. The melting or reflowing of the thermoplastic material of the opposed split webs can be brought about via the application of energy to the thermoplastic via inductive heating, Ohmic heating, laser absorption, or other heating methods. The heating of the thermoplastic can be via direct application of energy to the thermoplastic or via indirect application of energy to the thermoplastic such as, for example, direct application of energy to the conductor elements 64, which in turn melts or reflow the thermoplastic at those areas of contact between the conductor elements and the thermoplastic.

In one embodiment, the heating, and the associated melting or reflowing of the thermoplastic material of the opposed split webs, can occur immediately prior to the opposed split webs 66A, 66B being compressed together about the conductor elements 64 of the conductor-base assemblies 72 by the pressure platens 76A, 76B being compressed together.

In one embodiment, the heating, and the associated melting or reflowing of the thermoplastic material of the opposed split webs, can occur while the opposed split webs 66A, 66B are being compressed together about the conductor elements 64 of the conductor-base assemblies 72 by the pressure platens 76A, 76B being compressed together.

Figure 9:
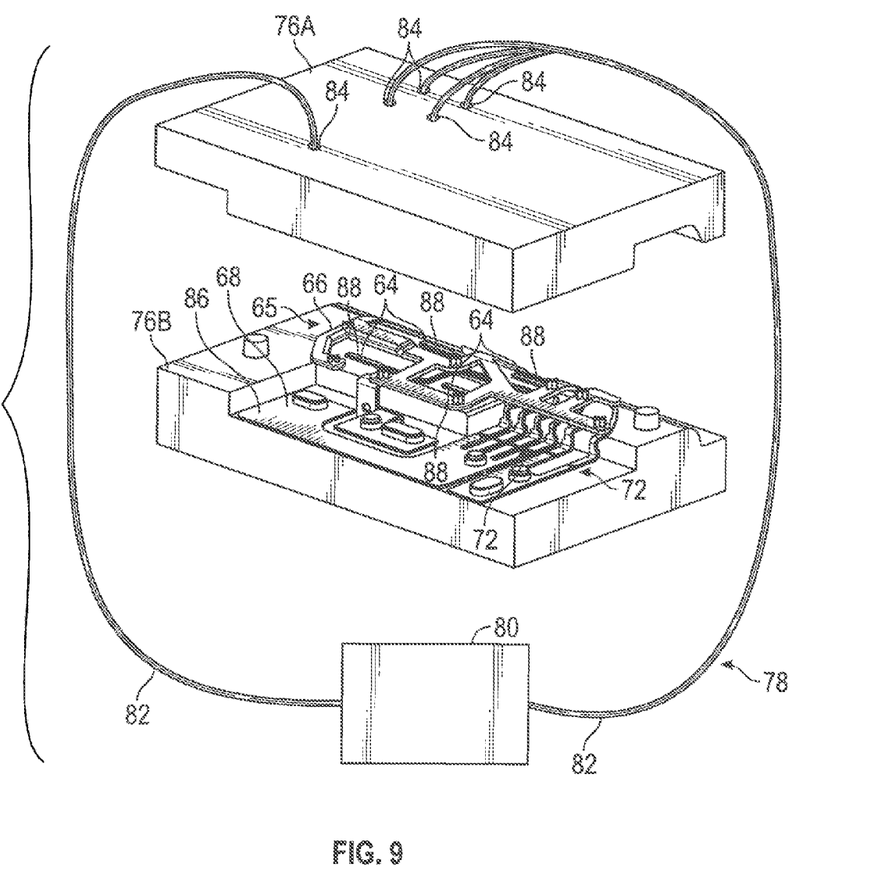
FIG. 9 is an isometric view of an example fusing system that melts or reflows the thermoplastic material of the opposed split webs while the opposed pressure platens are compressing the opposed split webs and the conductor elements together to cause the split webs and the conductor elements to fuse together.

FIG. 9 is an isometric view of an example fusing system 78 that melts or reflows the thermoplastic material of the opposed split webs 66A, 66B while the opposed pressure platens 76A, 76B are compressing the opposed split webs and the conductor elements 64 of the conductor-base assemblies 72 together to cause the split webs and the conductor elements to fuse together and form the fused thermoplastic-conductor subassembly 65 of FIG. 5. As shown in FIG. 9, the system 78 includes a power supply 80 electrically coupled via electrical conductors 82 to pogo pins 84 that extend through the upper pressure platen 76A. Each pogo pin 84 makes electrical contact with a respective common or ground contact 86 on a base 68 of a conductor-base assembly 72 or a power contact 88 on a specific conductor element 64 of the conductor-base assembly 72. Via the power supply and the network of conductors electrically coupled to the base 68 and conductor elements 64 of a conductor-base assembly 72, the conductor-base assembly 72 can be heated via Ohmic heating while the pressure platens 76A, 76B compressively sandwich together the thermoplastic split webs 66A, 66B about the conductor elements 64. The elevated temperature of the conductor elements 64 provides the heat to melt or reflow the thermoplastic material of the split webs to cause the thermoplastic material to fuse about the conductor elements 64 and the split webs 66A, 66B to fuse together, thereby forming the fused thermoplastic-conductor subassembly 65 of FIG. 5.

Once the thermoplastic material has sufficiently cooled, the fused thermoplastic-conductor subassembly 65 of FIG. 5 can be removed from the system 78 of FIG. 9 [block 140]. The blocks 44, 46 can then welded to the conductor elements 64 to form the connector assembly 42 of FIGS. 4A and 4B, after which the connector assembly 42 can be assembled into the header 40 via casting, injection molding, or other methods to form the header connector assembly 22 of FIG. 2. The header connector assembly is coupled to the housing 24 of the IPG 20 via methods known in the art.

Figure 10:
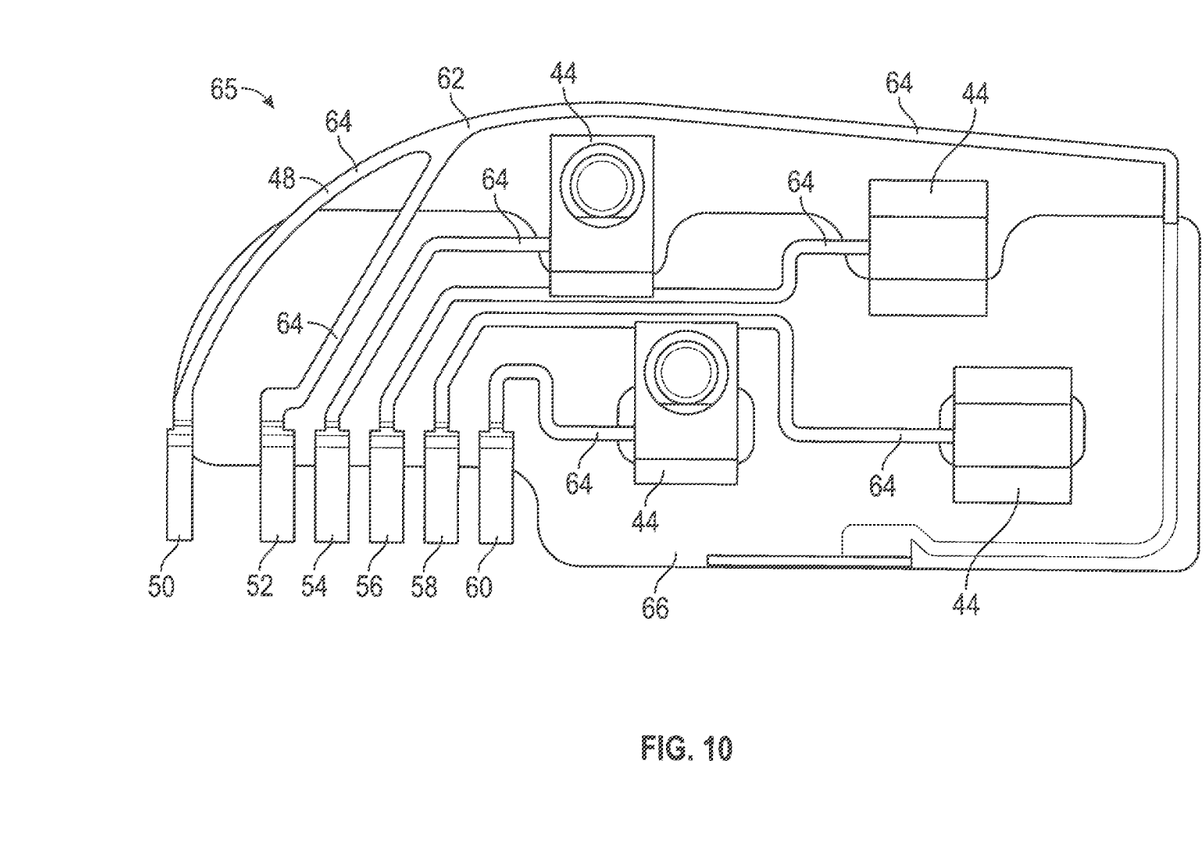
FIG. 10 is an isometric view of another fused thermoplastic-conductor subassembly 65.

While, as discussed above with respect to FIGS. 5-9, the fused thermoplastic-conductor subassembly 65 may be the result of a manufacturing process wherein the conductor elements 64 are sandwiched between a pair of opposed split webs 66A, 66B that are fused together and about the conductor elements, in other embodiments, the fused thermoplastic subassembly 65 may be manufactured via other methods and have other configurations. For example, as depicted in FIG. 10, which is an isometric view of another fused thermoplastic-conductor subassembly 65, the subassembly 65 includes blocks 44, 46, electrical conductor elements (e.g., wires, traces, or other electrical conductors) 64 associated with the antenna 48, RF anchor tab 50, RF pin tab 52, A-tip tab 54, A-ring tab 56, RV-ring tab 58, RV-tip tab 60, and ribbon carrier 62 of the connector assembly 42 of FIGS. 4A-4B, plus a thermoplastic structure 66 fused with portions of the conductor elements 64 at certain locations of the conductor elements 64 and, in some instances, the blocks 44, 46. The thermoplastic structure 66 of this embodiment may be in the form of a single thermoplastic plate or sheet. In one embodiment of this subassembly 65, because the blocks 44, 46 are welded to the conductor elements 64 prior to the thermoplastic being fused to the conductor elements, the blocks 44, 46 are included, eliminating the need for subsequent attachment.

The fusing of the thermoplastic structure 66 with the conductor elements and blocks maintains a desired spacing between the conductor elements 64 and blocks 44, 46. This desired spacing is one that is preferred during the manufacturing of the connector assembly 42 from the conductor elements 64 and the combining of the connector assembly 42 with the header 40 of the header connector assembly 22 to form the header connector assembly 22, the combining of the connector assembly 42 with the header 40 involving a backfilling process, an overmolding process, an injection molding process or another manufacturing process.

Figure 11:
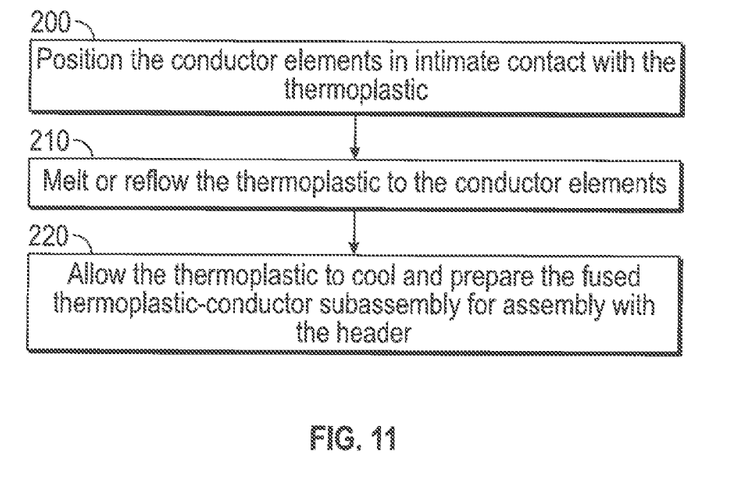
FIG. 11 is a flow chart outlining a method of manufacturing the fused thermoplastic-conductor subassembly of FIG. 10.
Figure 12:
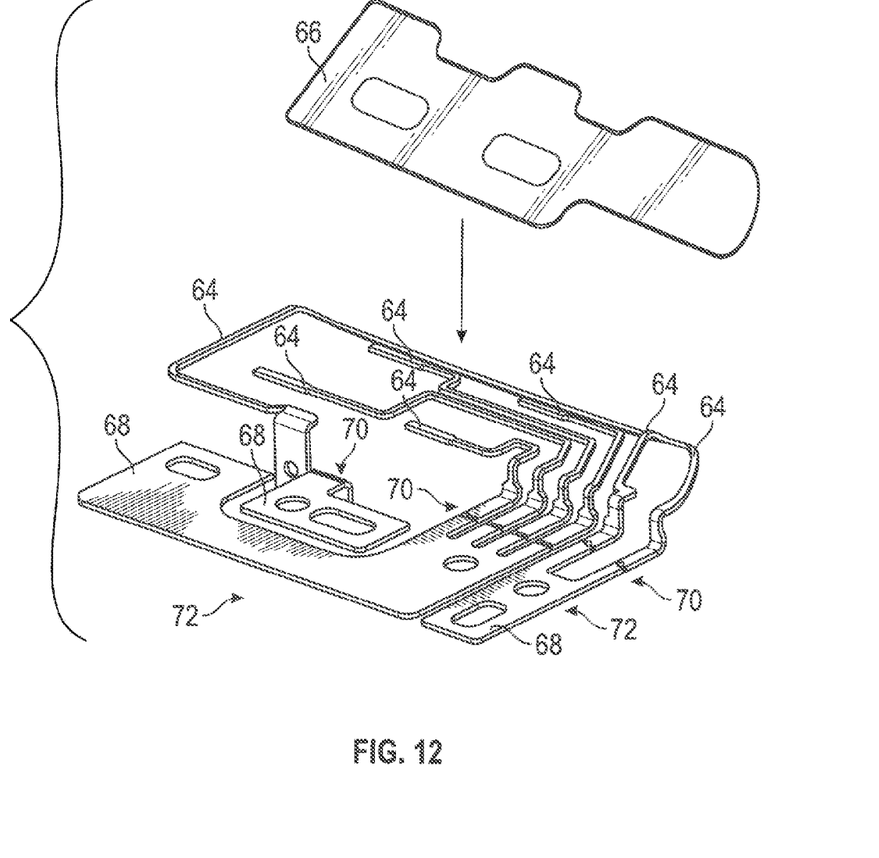
FIG. 12 is the same view as FIG. 10, except the thermoplastic structure has yet to be fused to the conductor elements.

To begin a discussion of the manufacture of the fused thermoplastic-conductor subassembly 65 of FIG. 10, reference is made to FIGS. 11 and 12. FIG. 11 is a flow chart outlining the manufacturing process, and FIG. 12 is the same view as FIG. 10, except the thermoplastic structure 66 has yet to be fused to the conductor elements 64. As can be understood from FIGS. 10 and 12, the conductor elements 64 are initially maintained in position relative to each other via regions or bases 68 of excess or scrap conductive material from which the conductor elements 64 are printed, etched, stamped, etc. These excess or scrap regions or bases 68 are removed from the conductor elements 64 at separation lines 70 at a point in the assembly subsequent to the fusing of the webs 66A, 66B about the conductor elements 64. For purposes of this discussion, when the conductor elements 64 are positioned relative to each other via the attached regions or bases 68 prior to the regions or bases 68 being removed from the conductor elements 64, the combined conductor elements 64 and regions or bases 68 are referred to herein as a conductor-base assemblies 72.

As can be understood from FIGS. 11 and 12, in one embodiment, the conductor-base assemblies 72 are positioned adjacent the thermoplastic structure 66 such that the thermoplastic structure is in intimate contact with the conductor elements 64 and/or portions of the blocks 44, 46 [block 200]. The thermoplastic structure 66 may be formed of thermoplastic materials such as, for example, TECOTHANE, PELLETHANE, BIONATE, ELASTHANE, or etc.

Optionally and similar to as discussed above with respect to FIGS. 5-9, pressure platens or other fixtures may be employed to maintain the intimate contact between the thermoplastic structure 66 and the conductor elements 64 and/or portions of the blocks 44, 46. The thermoplastic material of the thermoplastic structure 66 is melted or caused to reflow about the conductor elements 64, thereby fusing, if not imbedding, the conductor elements 64 in the thermoplastic material in at least a few locations on the conductor elements [block 210]. The melting or reflowing of the thermoplastic material of the thermoplastic structure 66 can be brought about via the application of energy to the thermoplastic via inductive heating, Ohmic heating, laser absorption, or other heating methods. The heating of the thermoplastic can be via direct application of energy to the thermoplastic or via indirect application of energy to the thermoplastic such as, for example, direct application of energy to the conductor elements 64, which in turn melts or reflow the thermoplastic at those areas of contact between the conductor elements and the thermoplastic.

Once the thermoplastic material has sufficiently cooled, the fused thermoplastic-conductor subassembly 65 of FIG. 10 can be readied for combination with the header 40 via casting, injection molding, or other methods to form the header connector assembly 22 of FIG. 2 [block 220]. The header connector assembly is coupled to the housing 24 of the IPG 20 via methods known in the art.

As mentioned above with respect to the embodiment of FIGS. 5-9 and the embodiment of FIGS. 10-12, the thermoplastic material 66 may be heated by inductive heating or by passing a current through the conductor elements 64 (Ohmic heating). Due to the use of electrical power, any compression platens 76A, 76B or other fixtures will be made of heat-resistant, non-conductive materials, such as, for example, polyetheretherketone ("PEEK"), Polytetrafluoroethylene ("PTFE"), ceramic, or etc.

In the case of inductive heating, an AC magnetic field is generated surrounding the conductor elements 64 to induce electrical eddy currents which heat the conductor elements 64. The methods for generating such a magnetic field take into consideration the complicated geometry of the conductor elements 64. Magnetic field generation can be incorporated locally into the platens 76A, 76B or by a device external to the platen assembly.

In the case of Ohmic heating, an AC or DC electrical current is passed through each conductive path of the conductor elements 64. Energy lost due to resistance of the material of the conductor elements generates heat. The temperature is controlled by voltage and current. Because there are multiple conductive paths, Ohmic heating will employ multiple connections. The base 68 of the conductor-base assembly 72 may be used as a common connection, and an electrical connection with the termination end of each conductor element 64 is made.

Also as mentioned above with respect to the embodiment of FIGS. 5-9 and the embodiment of FIGS. 10-12, the thermoplastic material 66 may be heated by the application of laser energy that is absorbed primarily by the conductor elements 64. In its simplest application, the laser energy can be directly focused onto the metal (e.g. titanium) forming the conductor elements 64. Because most clear thermoplastics have minimal absorption of 1 um to 2 um laser energy, lasers of these wavelengths can be directed through the thermoplastic plate and onto the titanium below. The laser energy can also be passed through glass or other optically clear platens or other fixtures, as needed. Surface roughed conductor elements 64 will absorb laser energy much more effectively.

Regardless of how the fused thermoplastic-conductor subassembly 65 manufactured, it will need to be incorporated into a final device 20. In one embodiment, the final step is a header over-molding process which may also incorporate additional mechanical components (e.g. header blocks, connectors, etc.). Final header over-molding can be done by epoxy-based cast in place methods as a stand-alone "pre-molded header" or directly onto the titanium device can 24. A "premolded" header can also be prepared by thermoplastic injection molding methods, where the fused thermoplastic-conductor subassembly 65 is inserted into the mold cavity prior to injection molding. If the header 40 is "premolded", it will have to be attached to the titanium can 24 using adhesives and possibly mechanical anchors. Electrical connections will also have to be made by welding or an appropriate connector.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A method of manufacturing an implantable electronic device, the method comprising:
   forming a fused thermoplastic-conductor subassembly by causing an electrically conductive component of a connector assembly of a header connector assembly to fuse to a thermoplastic; and
   forming a header of the header connector assembly about the fused thermoplastic-conductor subassembly;
   wherein the thermoplastic comprises at least two opposed portions and the electrically conductive component is sandwiched between the two opposed portions prior to the electrically conductive component being fused to the thermoplastic.

2. The method of claim 1, wherein the fusing is brought about by melting the thermoplastic via at least one of inductive heating, Ohmic heating or laser heating of the electrically conductive component.

3. The method of claim 1, wherein the thermoplastic comprises at least one of Tecothane, Pellethane, Bionate or Elasthane.

4. The method of claim 1, wherein the electrically conductive component comprises at least one of a wire, ribbon, antenna, block, or ring.

5. The method of claim 1, wherein the header is formed about the thermoplastic-conductor subassembly via at least one of a backfilling process, an overmolding process, an injection molding process, or a casting process.

6. The method of claim 1, wherein the sandwiched opposed portions and electrically conductive component are compressed between pressure platens when the electrically conductive component is being fused to the thermoplastic.

7. The method of claim 1, wherein the resulting implantable electronic device comprises an implantable pulse generator for administering electrotherapy via an implantable medical lead configured to couple with the implantable pulse generator.

8. The method of claim 1, wherein the resulting implantable electronic device comprises an implantable cardiac monitor.

\* \* \* \* \*